(12) United States Patent
Van Velsor et al.

(10) Patent No.: US 8,170,809 B2
(45) Date of Patent: *May 1, 2012

(54) GUIDED WAVES FOR NONDESTRUCTIVE TESTING OF PIPES

(75) Inventors: Jason K. Van Velsor, State College, PA (US); Steven E. Owens, Bellefonte, PA (US); Joseph L. Rose, State College, PA (US)

(73) Assignee: FBS, Inc., State College, PA (US)

( * ) Notice: Subject to any disclaimer, the term of this patent is extended or adjusted under 35 U.S.C. 154(b) by 601 days.

This patent is subject to a terminal disclaimer.

(21) Appl. No.: 12/271,412

(22) Filed: Nov. 14, 2008

(65) Prior Publication Data

US 2009/0150094 A1 Jun. 11, 2009

Related U.S. Application Data

(60) Provisional application No. 60/987,864, filed on Nov. 14, 2007.

(51) Int. Cl.
*G01N 29/04* (2006.01)
(52) U.S. Cl. ........................................................ 702/39
(58) Field of Classification Search .................... 702/39
See application file for complete search history.

(56) References Cited

U.S. PATENT DOCUMENTS

| | | | |
|---|---|---|---|
| 4,055,990 A | 11/1977 | Topping | |
| 4,127,035 A | 11/1978 | Vasile | |
| 4,439,730 A | 3/1984 | Kaufman | |
| 4,769,598 A | 9/1988 | Krieg et al. | |
| 4,945,306 A | 7/1990 | Lowther | |
| 5,054,490 A * | 10/1991 | Rossman et al. | 600/449 |
| 6,404,189 B2 | 6/2002 | Kun et al. | |
| 7,751,989 B2 * | 7/2010 | Owens et al. | 702/33 |

FOREIGN PATENT DOCUMENTS

| | | |
|---|---|---|
| EP | 0304053 B1 | 2/1989 |
| EP | 0389877 A | 10/1990 |

* cited by examiner

*Primary Examiner* — Tung S Lau
(74) *Attorney, Agent, or Firm* — Duane Morris LLP (57) ABSTRACT

A method for the nondestructive testing of pipeline, and internal or external coatings, using guided ultrasonic waves excited from the inside or outside diameter, wherein at least two transducers are employed to send and receive ultrasound, wherein a data normalization scheme is employed to account for transducer variability, and wherein the hardware arrangement has a number of pulser channels and a number of receiver channels for the collection and storage of signals.

20 Claims, 8 Drawing Sheets

GUIDED WAVES FOR NONDESTRUCTIVE TESTING OF PIPES

CROSS REFERENCE TO RELATED APPLICATIONS

The present application claims priority under 35 U.S.C. §119(e) to U.S. Provisional Patent Application 60/987,864 filed on Nov. 14, 2007, the entirety of which is incorporated by reference herein.

FIELD OF THE INVENTION

Aspects of the invention relate to pipeline inspection. More specifically, aspects of the invention relate to providing a guided wave pipeline inspection system and method with enhanced coating disbond detection, corrosion detection and crack sizing capabilities.

BACKGROUND INFORMATION

Corrosion is one of the primary preventable causes of failure in transmission pipelines. Protective coatings serve as the first barrier against this phenomenon. Once a coating is compromised, it is only a matter of time before corrosion begins.

The Magnetic-Flux Leakage (MFL) method is currently the dominant technology for the in-line inspection (ILI) of transmission pipeline. Because the MFL ILI method depends on the ferrous nature of the material being inspected, it is only capable of detecting the effect of the corrosion problem and not the cause; a failure of the protective coating. Furthermore, MFL methods can potentially miss crack-like defects and have a large tolerance and low certainty for sizing metal-loss defects, such as corrosion.

The ability to reliably detect coating disbonds would represent a significant contribution to the pipeline integrity management sector as it would enable preventative maintenance action prior to the development of corrosive metal loss defects. In the event that defects are already present, a method of reliably detecting cracking and more accurately sizing metal-loss defects would also be a welcome contribution.

To prevent the onset of corrosion and to identify critical regions where corrosion may have already initiated, there is a need for a reliable, robust, multi-feature coating disbond detection technique that is applicable over a range of coating types and thicknesses. For regions that already contain defects, there is a present need for more accurate detection and sizing capabilities.

Furthermore, there is a need for a coating disbond detection technique and apparatus that will not be confounded by moderate wall thinning, diametral variations, and wetted/soiled coating interfaces and for a defect sizing technique that is highly sensitive to wall losses and cracking.

Furthermore, there is a need for a sensor arrangement and data acquisition technique that is relatively low cost and capable of withstanding the rigors encountered in an ILI environment.

SUMMARY

It is therefore an objective of an aspect of the invention to provide a reliable method and apparatus for detecting coating disbonds using a multi-feature algorithm.

It is also an objective of an aspect of the invention to provide a more accurate and reliable method for crack and corrosion sizing than is presently available through the employment of guided-wave focusing in real-time, synthetically, and/or geometrically and through the employment of pattern recognition approaches.

It is also an objective of an aspect of the invention to provide said capabilities in a package that is capable of withstanding the rigors of a typical ILI environment.

It is also an objective of an aspect of the invention to provide disbond detection capabilities for a range of coating types and thicknesses without being confounded by moderate wall thinning, diametral variations, and wetted/soiled interfaces.

Another objective of an aspect of the invention is to improve upon conventional technology through the employment of newly identified coating disbond detection features, newly developed data processing techniques for ILI using guided waves, newly developed guided-wave focusing capabilities for ILI, and newly developed pattern recognition algorithms.

The objectives are achieved as illustrated and described. In an example embodiment of the invention, an ultrasonic guided-wave nondestructive testing method for coating disbond detection is presented, comprising: a mode selection routine, a self-calibrating sensor arrangement, a set of extracted wave features, and signal enhancement methods, wherein the bond state of internal or external pipe coatings, or both, may be characterized.

In a further example embodiment, the system is configured to acquire data at fixed intervals while moving through a pipe.

In a further example embodiment, the system configured for disbond detection uses a guided wave mode and frequency that exhibits dominant in-plane particle displacement, so to be sensitive to coating presence, or lack thereof, and is insensitive to moderate wall thinning, diametral variation, and wetted/soiled interfaces.

In a further example embodiment, the system for disbond detection may be configured such that a minimum of two sensors are required for the full circumferential inspection of a pipe at a particular axial location when employing circumferential guided waves. Sensors may comprise EMATs, piezoelectric transducers, or any other device capable of generating ultrasound in the pipe wall. Examples of EMATs may be, as non-limiting examples, Lorentz Type and Magnetostrictive Type sensors. The EMAT's may be pulsed or permanent magnet types.

In another example embodiment, the system for disbond detection may be configured such that a minimum of three sensors are required for the partial circumferential inspection of a pipe over some axial distance, as determined by the sensor separation, when employing axial guided waves. In this example embodiment, multiple sensor sets are required to achieve full circumferential inspection over some axial distance determined by the sensor separation.

In a further example embodiment, the system for disbond detection is configured such that all extracted signal features are measured relative to the induced wave as received by a receiver juxtaposed to the transmitting sensor.

In a yet further example embodiment, the system for disbond detection is configured such that the arrangement configured to send, receive and store signals uses an algorithm that minimizes data collected from the pipe.

In another example embodiment, the system for disbond detection may be configured such that a receiving sensor is exactly opposed the transmitting sensor, wherein constructive interference of the CW and CCW propagating waves result in the formation of a single received wave packet for bare or perfectly coated pipe. Deviations from perfect constructive interference can be used to characterize the coating bond state.

The objectives are achieved as illustrated and described. In an example embodiment of the invention, an ultrasonic guided-wave nondestructive testing method for crack and metal-loss defect sizing using a real-time, synthetic, and/or geometric focusing technique is presented, comprising at least two transducers; an arrangement configured to send, receive, and store signals, wherein the arrangement has a number of pulser channels and a number of receiver channels, wherein the arrangement has at least one multiplexing arrangement for multiplexing signals from the arrangement; and a time delay arrangement connected to the arrangement configured to send, receive and store signals, the time delay arrangement configured to calculate and/or recall delay times for activation of the at least two transducers and activate the arrangement configured to send and receive signals for the at least two transducers based upon the delay times.

In a further example embodiment, the array geometry may be arranged so to achieve focusing in the circumferential direction, axial direction, or in both directions.

In a still further example embodiment, the array may contain as few as two sensors and a maximum number limited by the smaller of two numbers: the maximum number physically permitted by the pipe geometry, or the maximum number permitted by the utilized electronics.

In a yet farther example embodiment, the time-delay and amplitude weightings required for real-time phased-array focusing may be computed onboard or may be stored in an onboard library, wherein focal points are predetermined or fed to the system from other data sources, which may include, but are not limited to, guided wave, MFL, and Eddy Current data.

Additionally, in an example embodiment, correction of the time-delay and amplitude weights may be made to account for the motion of the ILI tool. Corrections are based on the velocity of the tool relative to the desired focal point, wherein the altered path length can be used to adjust the time-delays and amplitude weights. This correction may not be required but may result in enhanced focusing results.

In a further example embodiment, the spatial orientation of the array sensors used for geometrical focusing is predetermined by the desired focal point and mode and frequency of inspection.

In an example embodiment of the invention, a pattern recognition approach may be employed which has, as inputs, occurrences and values of wave phenomena such as, but not limited to, mode conversion phenomena, scattering phenomena, transmission and reflection factors, phase features, and time-of-flight and amplitude features, wherein the algorithm inputs are compared to predetermined trends and, as output, a prediction is made concerning the type of defect detected, location of defect and the approximate size of one or more of the defect dimensions. The pattern recognition algorithm inputs are not limited to ultrasonic data, but may include data from any other test method, such as, but not limited to, MFL or Eddy Current data.

In another example embodiment of the invention, an ultrasonic guided-wave nondestructive testing method for a pipe is presented. In this example embodiment, the method provides for placing an array of transducers on the pipe; placing a self calibrating sensor arrangement on the pipe, generating a wave through the transducers from a mode selection routine operable on a computer to select a mode of excitation for the array of transducers; receiving the wave through the sensor arrangement and processing the wave through a signal receiving routine operable on the computer, the computer configured to operate with the self-calibrating sensor arrangement and receive the wave from the array of transducers, and processing the wave through the computer through a signal enhancement process; wherein at least one of a bond state of internal and external pipe coatings are characterized through the signal enhancement process and any present coating disbonds are detected and sized approximately.

In another example embodiment, a guided-wave sensor array and system for the approximate sizing of corrosion and cracking in pipe using at least one of a real-time, synthetic, and geometric focusing technique is presented comprising: at least two transducers, an arrangement configured to send, receive, and store signals, wherein the arrangement has a number of pulser channels and a number of receiver channels, wherein the arrangement has at least one multiplexing arrangement for multiplexing signals from the arrangement; and a time delay arrangement connected to the arrangement configured to send, receive and store signals, the time delay arrangement configured to at least one of calculate and recall delay times for activation of the at least two transducers and activate the arrangement configured to send and receive signals for the at least two transducers based upon the delay times.

DETAILED DESCRIPTION

Figure 4:
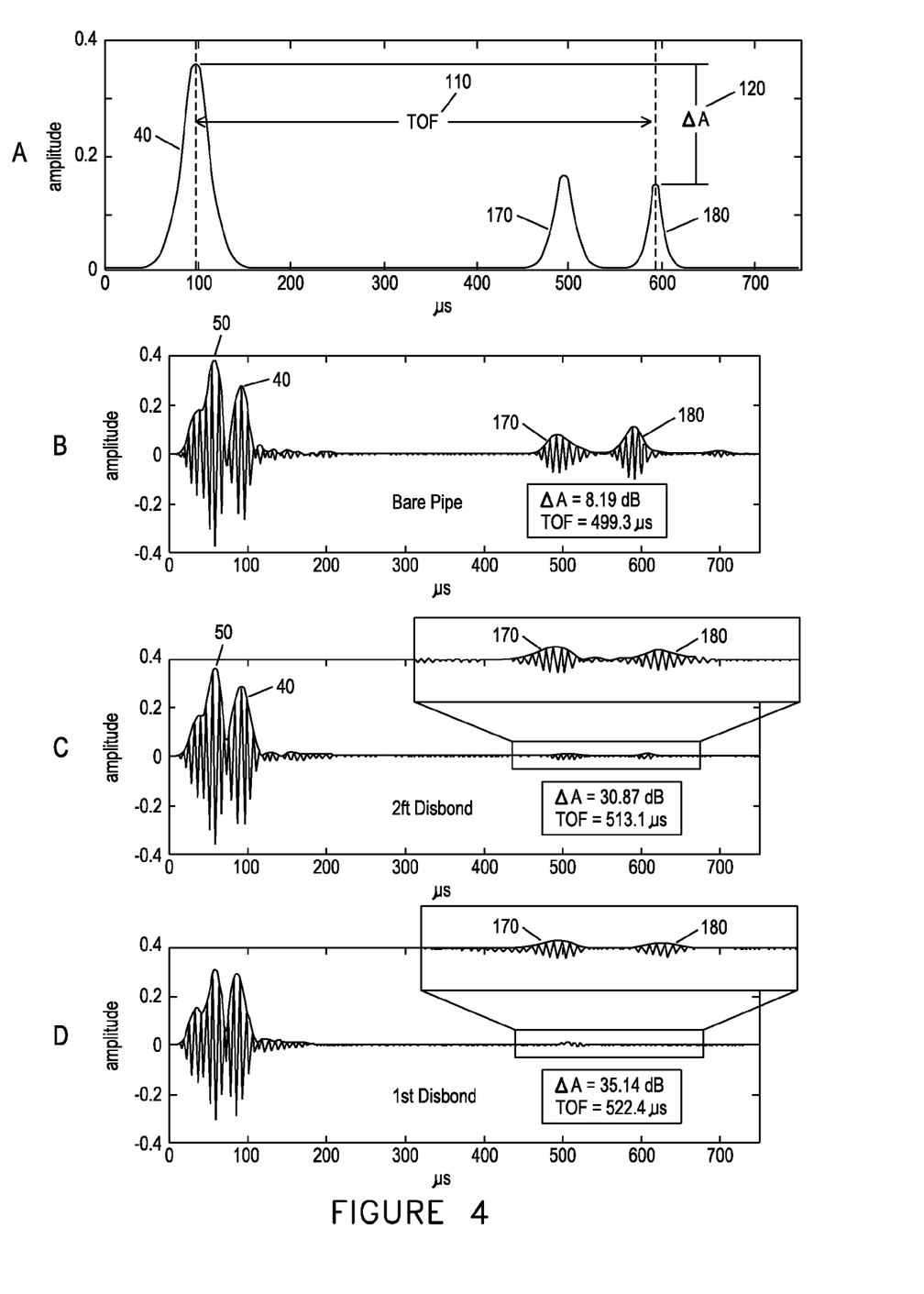
FIGS. 4A, 4B, 4C, and 4D illustrate how coating disbond detection and size estimation is done using a sensor configuration as seen in FIG. 3A. Experimental results for the detection of differently sized coating disbonds in a 20 in. Schedule 10 pipe with a 3 mm coal-tar coating using the 130 kHz SH1 wave mode.
Figure 5:
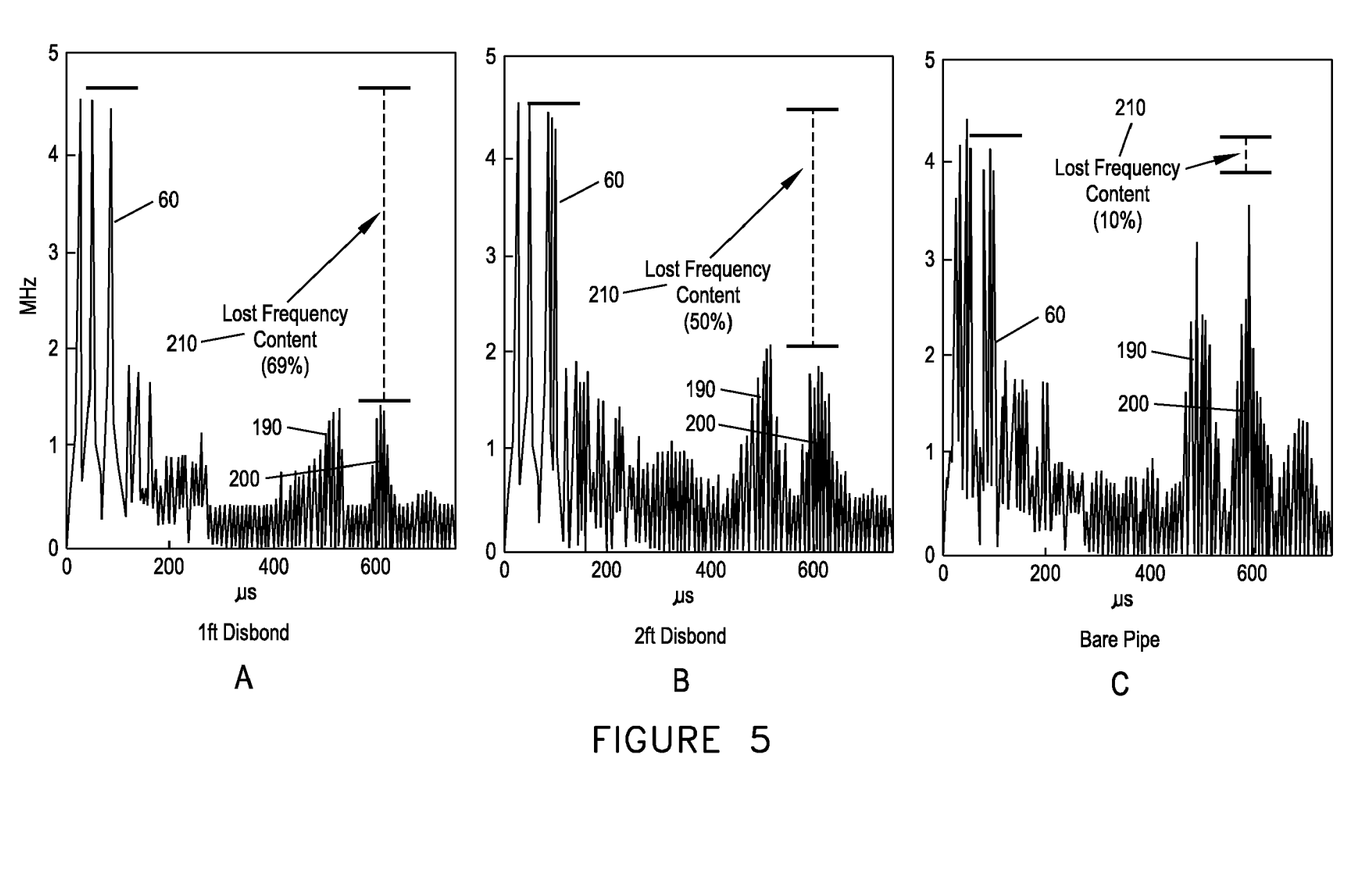
FIGS. 5A, 5B, and 5C contain experimental results for the detection of differently sized coating disbonds in a 20 in. schedule 10 pipe with a 3 mm coal-tar coating using the 130 kHz SH1 wave mode. Frequency-based disbond detection features are detailed.

Referring to FIGS. 3A, 3B, 3C and 3D, in an example embodiment of the invention, an apparatus for implementing a method is developed for the inspection of a coated pipe 10 in which a transmitting sensor 20 and a receiving sensor 30 are separated by some short fixed distance. Referring to FIGS. 4A, 4B, 4C and 4D, all signal features used for disbond detection are calibrated to a reference pulse 40 that travels directly from the transmitter 20 to the receiver 30. The pulse 50, seen in FIGS. 4B-4D, that arrives prior to the reference pulse 40 is electronic noise generated by the electromagnetic acoustic transducers (EMATs) used for excitation and reception. In an example embodiment, there is no specific requirement for the use of EMATs; any device that generates the desired guided-wave mode and frequency is applicable. Several coating disbond detection features are illustrated in the conceptual waveform shown in FIG. 4A. The time-of-flight ("TOF") 110 and amplitude disparity ("ΔA") 120 between the reference pulse 40 and the first complete circumferential traversal 180 may be used to identify and approximately size coating disbonds, as illustrated in FIGS. 4B-4D. Referring to FIGS. 5A, 5B and 5C, the time-frequency representation of the waveforms seen in FIGS. 4B-4D can be seen. Another disbond detection feature, the lost frequency content 210, is a measure of the relative difference between the frequency content of the reference pulse 60 and the first complete circumferential traversal 200. The remaining frequency content of the reference pulse 60 and first complete traversal 200 may be utilized. All disbond detection features described here may also be applied to the analysis of the partial circumferential traversal 170,190 though the results will not account for the region between the transmitter 20 and receiver 30. The time-frequency domain signal of the complete traversal pulse 200 may also be used to aid in the identification of low-amplitude pulses that are embedded in the noise of the time-amplitude representation.

Figure 7:
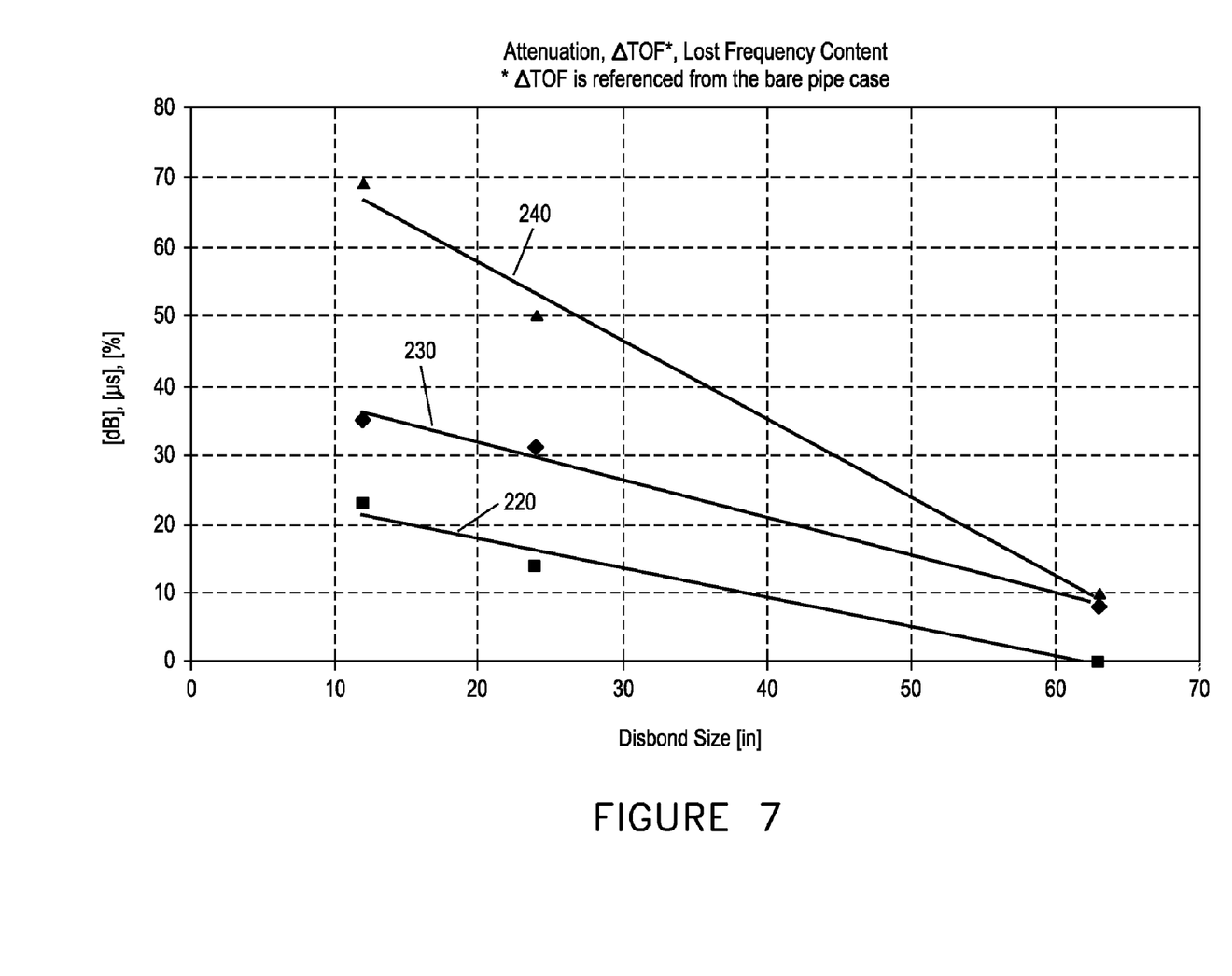
FIG. 7 shows several of the identified coating disbond detection features plotted on the same graph vs. disbond size, illustrating the disbond sizing estimate potential.

Referring to FIG. 7, in an example embodiment of the invention, the identified trends relating to coating disbond size are used to approximately size the coating disbonds. The change in time-of-flight ("ΔTOF") trend 220, the amplitude disparity trend 230, or the lost frequency content trend 240 may be used individually to estimate coating disbond size or through any combination of addition, subtraction, multiplication, and division of the trends. The sizing estimate routine is not limited to the feature trends shown in FIG. 7 but may employ trends from any of the features discussed herein.

Figure 3:
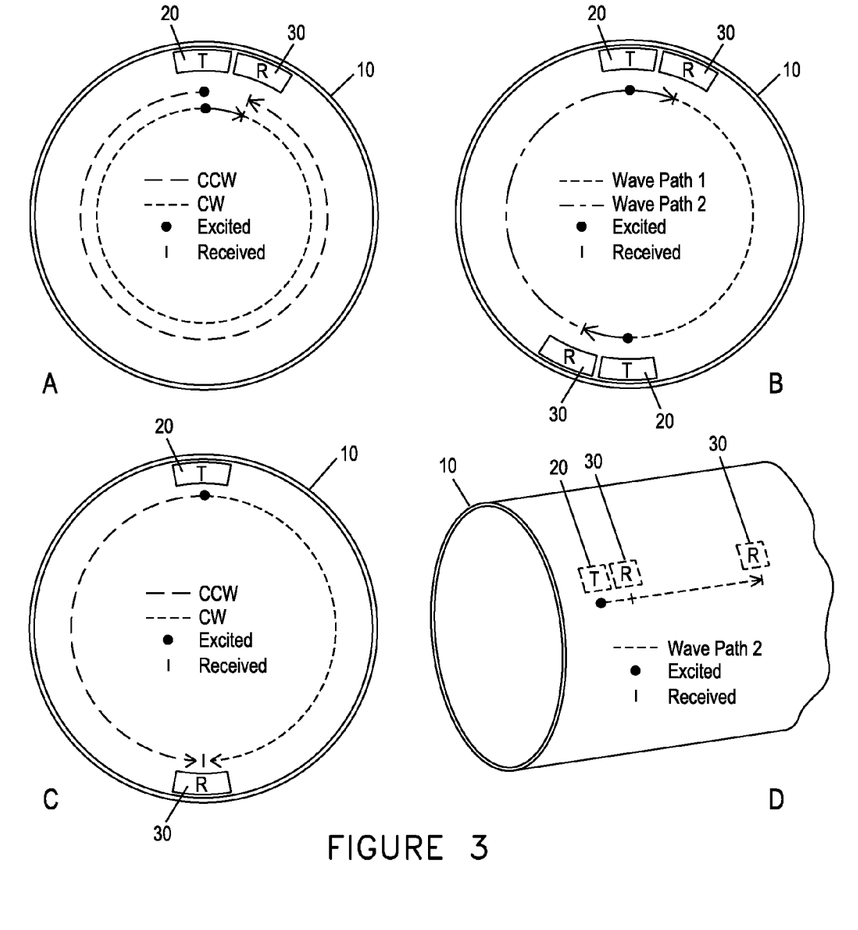
FIGS. 3A, 3B, 3C, and 3D contain illustrations of several different self-calibrating sensor arrangements for inspection using both circumferentially and axially oriented waves.

Referring to FIGS. 3A, 3B, 3C and 3D, multiple transmitter 20 and receiver 30 arrangements are possible. As seen in FIG. 3A, an example embodiment of the coating disbond detection technique may require as few as two sensors. In this configuration, a single transmitter 20 is used to generate a wave that travels directly to the receiver 30 and then once completely around the circumference of the pipe 10, arriving at the receiver 30 once again. Depending on the method of excitation, a wave traveling in the opposite direction may also be present but does not initially travel beneath the receiver and also does not traverse the entire circumference prior to first reception. In FIG. 3A, the clockwise going wave travels directly to the receiver 30 and then completely traverses the circumference of the pipe 10. The counter clockwise going wave does not.

For cases where high attenuation prevents sufficient propagation distances, or for cases in which increased circumferential resolution is desired, an example embodiment may employ the use of multiple transmitter 20 and receiver 30 pairs for disbond detection, as illustrated in FIG. 3B. In this configuration, a wave excited by a transmitter 20 travels directly to the nearest receiver 30, providing a reference pulse 40, then propagating around the circumference of the pipe 10 when it is again received by the next closest receiver 30. This configuration is not limited to two sensor pairs, as illustrated, but can include as many sensor pairs as can be physically accommodated given the geometrical constraints of the pipe 10.

Figure 6:
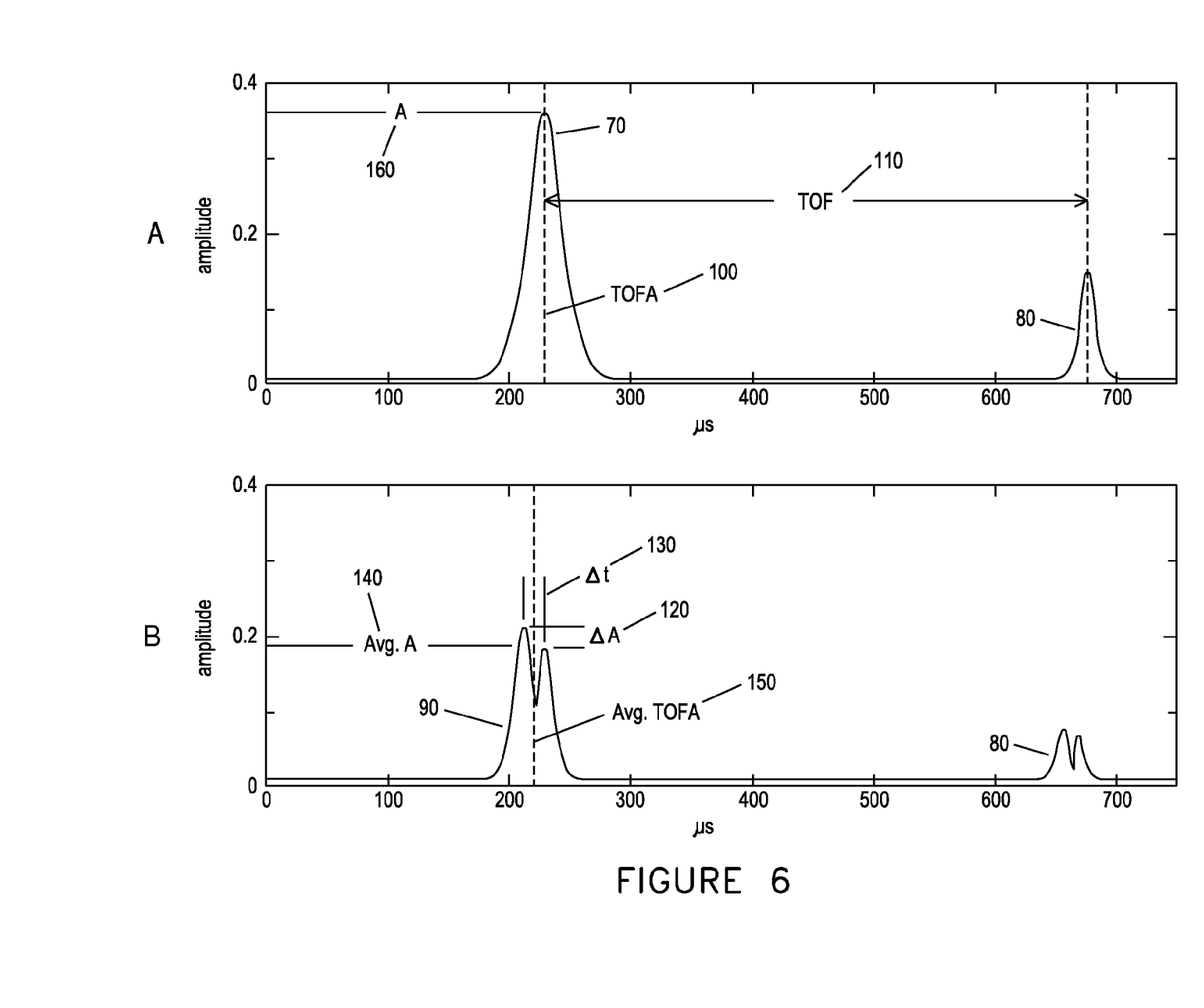
FIGS. 6A and 6B provide an illustrative example of how disbond detection is done using the constructive interference method as illustrated in FIG. 3D.

Referring to FIG. 3C, another example embodiment of the invention in which full circumferential inspection for coating disbonds is accomplished with two sensors and propagation distances as short as one half of the circumference of the pipe 10 is illustrated. In this configuration, the transmitter 20 simultaneously generates a clock wise and counter clock wise traveling wave. For the case of a coated pipe 10 or a completely bare pipe 10, the clock wise and counter clock wise traveling wave will constructively interfere in a region opposite the transmitter 20. The receiver 30 is placed in this region. Referring to FIGS. 6A and 6B, constructive interference, as would occur for a uniform coating or for a bare pipe 10, will result in the reception of only one perceived wave packet 70 whose amplitude contains contributions from both the clock wise and counter clockwise traveling waves (wave packet envelope is illustrated in figure). If not completely attenuated, subsequent pulses 80 from multiple traversals of the pipe circumference 10 may be received and utilized for measurement. This is also true of the configurations seen in FIGS. 3A and 3B. In the case of an asymmetrically distributed coating anomaly, the single perceived wave packet 70 will assume a multiple-peak packet 90 as provided in FIG. 6B. Features that may be utilized to identify and estimate the size of the coating disbond include the time-of-first-arrival ("TOFA") 100, the time-of-flight ("TOF") 110 between the first received wave packet 70,90 and subsequently received wave packets 80, the amplitude disparity 120 between the multiple peaks of the first wave packet 90, the arrival time disparity 130 between the multiple peaks of the first wave packet 90, the average amplitude 140 of the multiple peaks of the first wave packet 90, and the average TOFA 150 of the multiple peaks of the first wave packet 90. These same features can be examined for any or all subsequently received wave packets 80. In a further example embodiment, the amplitude 160, TOFA 100 of the wave packet 70, and TOF 110 between subsequently received waves 80, or multiples thereof may be used as a baseline if acquired in a known bare pipe region or known region of well bonded coating.

Figure 1:
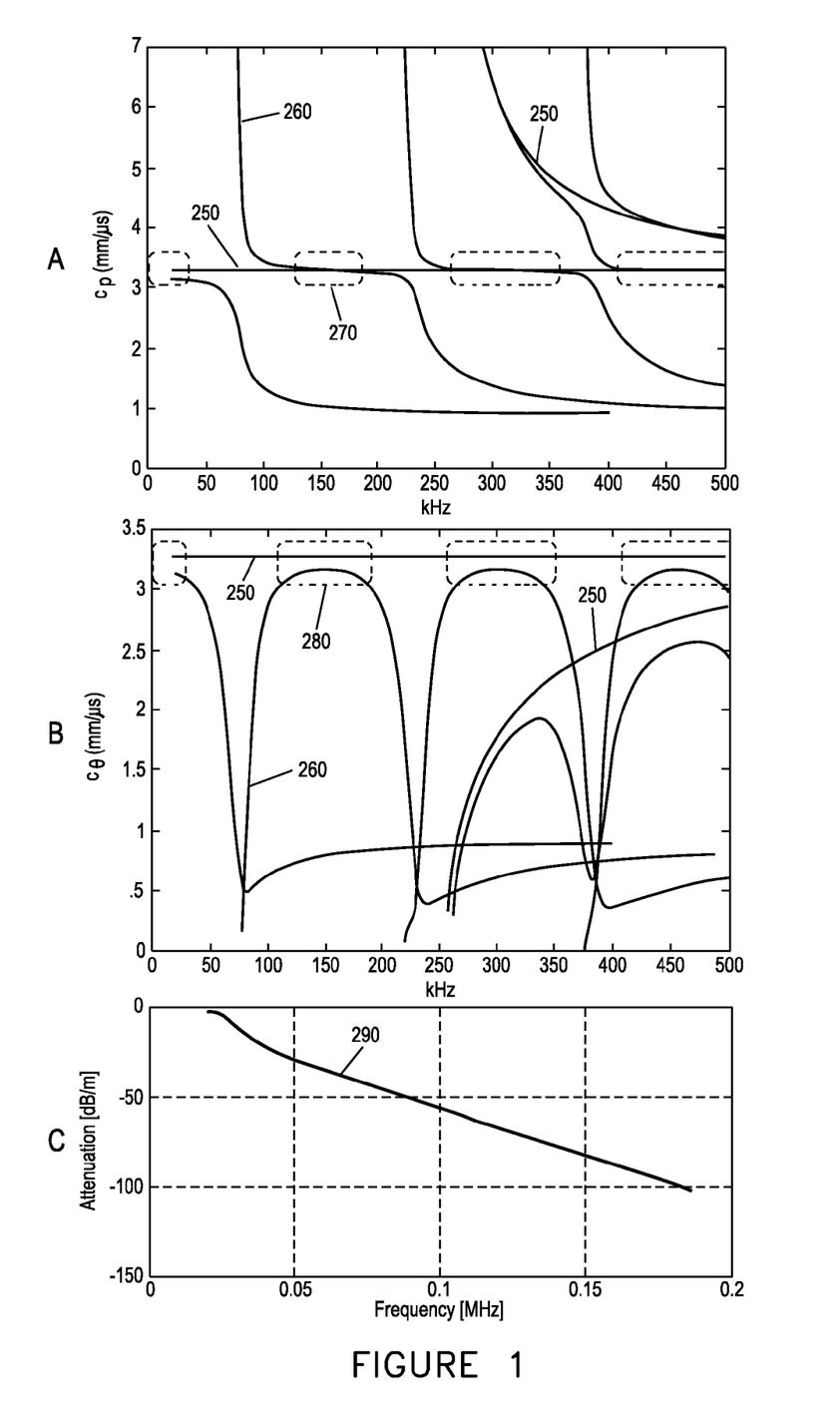
FIGS. 1A, 1B, and 1C are examples of phase velocity, group velocity, and attenuation dispersion curves, respectively, for circumferential shear horizontal (SH-) waves in bare and coated pipe.
Figure 2:
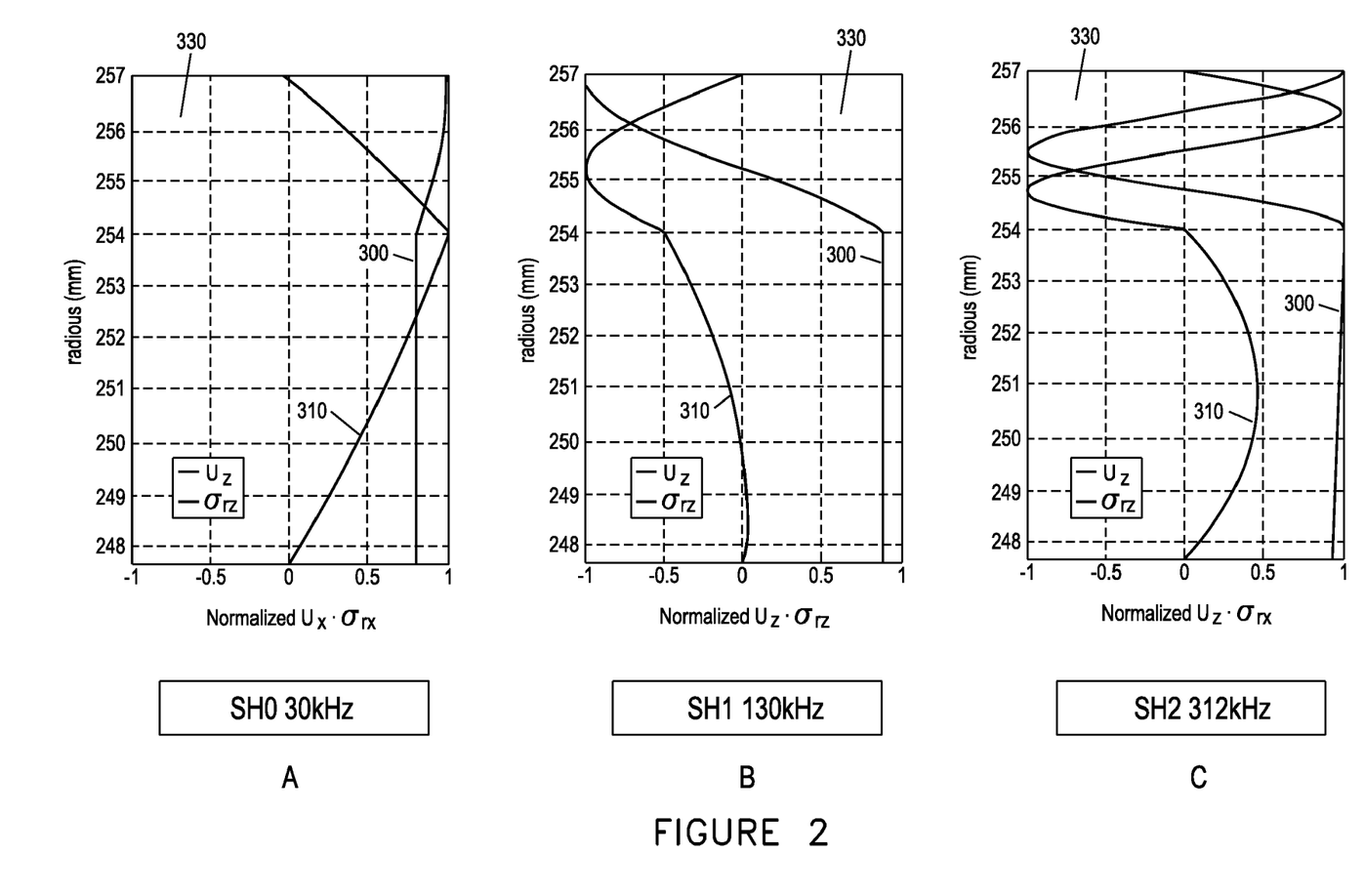
FIGS. 2A, 2B, and 2C are examples of wave structures for different circumferential SH-wave modes and frequencies in a coated pipe.

Referring to FIG. 1, in an example embodiment of the invention, the selected mode and frequency used for coating disbond inspection should be sensitive to the presence of coating, or lack thereof and should not be sensitive to variables often encountered in an inspection environment. These variables could include moderate wall thinning, diametral variations, and wetted/soiled coating interfaces. In this embodiment, the phase velocity dispersion curves for the bare pipe 250 (black line) and the coated pipe 260 are plotted. In FIG. 1, the phase velocity, group velocity, and attenuation dispersion curves are shown for the SH mode group. A unique feature of this mode group is that it exhibits entirely in-plane particle displacement, that ensures that energy is not leaked into water that may occur at a disbond interface and minimizes losses into moisture containing soils. Lamb-type modes with dominant in-plane displacements also meet these criteria. Furthermore, the coated pipe curves 260 will converge, temporarily, to the bulk shear-wave velocity of the substrate to which the coating is applied, usually but not limited to steel. In these convergence regions 270, the wave structure in the pipe wall is similar for both the bare pipe and coated pipe cases. FIGS. 2A-2C illustrate the wave structures for modes and frequencies within the convergence regions 270. In these figures, the lines 300 correspond to particle displacement and the lines 310 correspond to shear stress. The ideal modes and frequencies have large particle displacements at the interface of the pipe 320 and the coating 330. This ensures sensitivity to the presence of the coating. It is seen that all mode/frequency combinations in FIG. 2 meet this criteria. Next, the group velocity dispersion curves seen in FIG. 1B show that, in these identified regions, the measurable wave velocity peaks at a value below the normal SH0 wave velocity in a bare pipe. Therefore, with the identified modes and frequencies, wave packets will travel more slowly in a coated pipe than in a bare pipe, resulting in a time-based disbond detection feature. Additionally, as seen in the attenuation dispersion curve shown in FIG. 1C, the presence of coating results in wave attenuation, providing an amplitude-based disbond detection feature. Furthermore, for the mode 290 shown in FIG. 1, it is seen that attenuation increases as a function of frequency. Therefore, coating will cause the higher frequency content of pulse to be attenuated more quickly than the lower frequency content, thus providing a frequency-based disbond detection feature. Essentially the coating is acting as a high-frequency filter with the amount of high frequency content being filtered dependent on the amount of coating present. This same concept is applicable to any attenuation trend that is either entirely increasing or entirely decreasing with frequency. Lamb-type modes are applicable.

Figure 8:
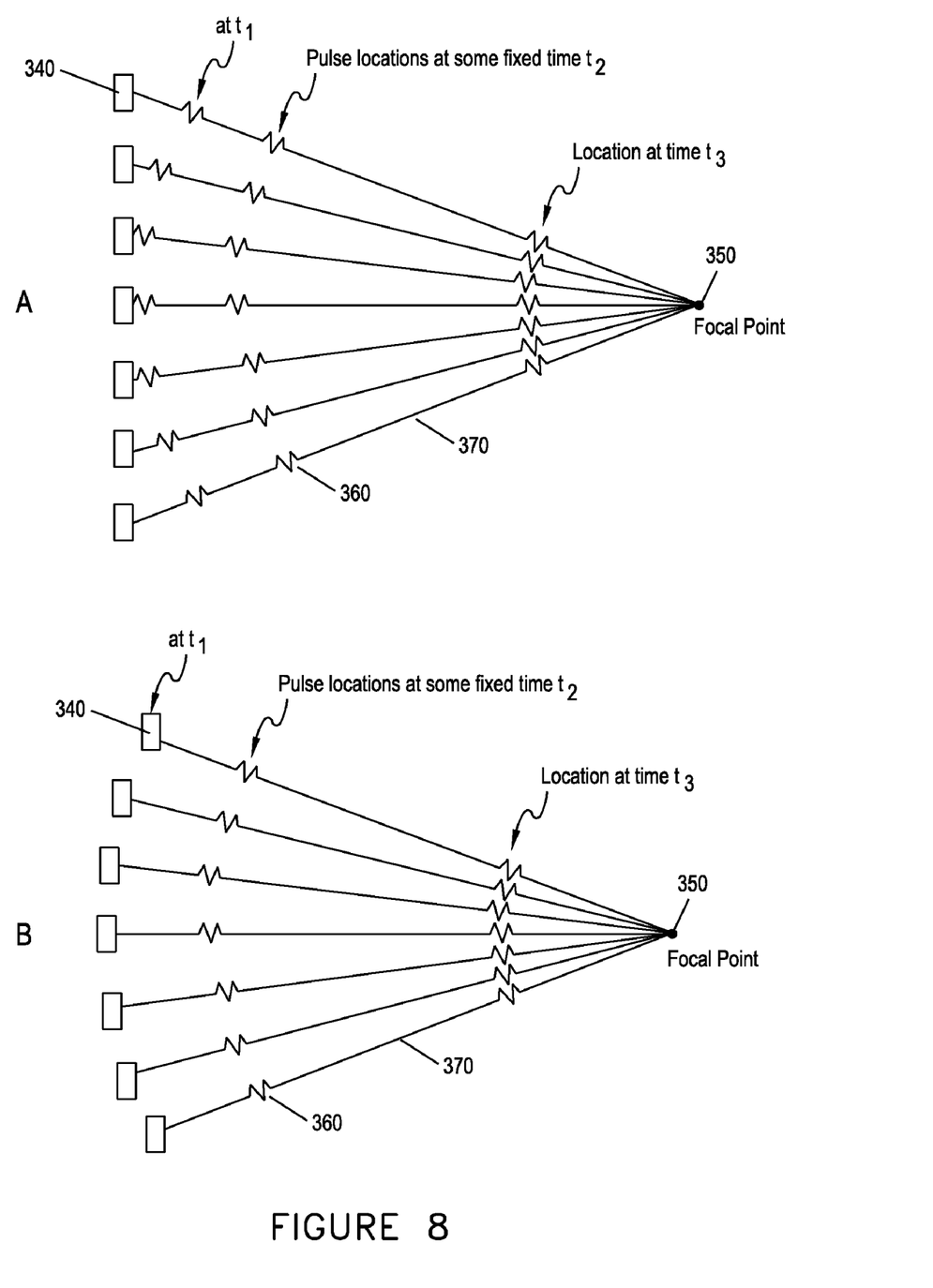
FIGS. 8A and 8B illustrate the phased/synthetic array and geometric approach to focusing guided waves.

Referring to FIGS. 8A and 8B, in an example embodiment of the invention, guided-wave focusing can be achieved through several methods. In the phased-array and synthetic focusing methods, an array of sensors 340 such as illustrated in FIG. 8A is employed, though the array may assume other shapes than the illustrated line. In the phased-array approach, time delayed and possible amplitude weighted pulses 360 are generated using the array sensors 340 which will converge constructively at some focal point 350, which need not be in the center of the array but may be skewed in some direction. The time delays and amplitude weights are calculated based on the mode and frequency excited and the path 370 to the focal point 350. All or some of the array sensors 340 may be used for the reception of wave reflections. In the case of a synthetic phased array, one sensor 340 is excited at a time and all other sensors 340 are used to receive reflections. Once all sender/receiver permutations are complete, time delays and amplitude weights are applied digitally, via post processing, to produce a focal point 350 at a desired location. The focal point 350 may then be digitally rastered to generate a C-scan image of the inspected area. In the case of a real-time phased-array, rastering may be employed but the size of the rastered region will depend on the data acquisition speed and ILI tool velocity. In FIG. 8B the geometric focusing concept is illustrated. In this method, the focal point 350 is determined by the relative spacing of the array sensors 340, which are all excited simultaneously.

In an example embodiment, a method to determine wave propagation features that are sensitive to coating failures is presented. Multiple detection features are necessary in order to create a robust and reliable disbond detection routine. Several potential features, including time, amplitude and frequency-based features are discussed.

Wave attenuation is one feature for the detection of coating disbonds. Because most protective coatings are visco-elastic in nature, a portion of the wave energy may be absorbed into the coating layer, resulting in a decrease in the amplitude of the received wave. Disbonds will therefore appear as an increase in wave amplitude. This phenomenon can be seen in the ultrasonic guided wave RF waveforms.

Because signal amplitude will vary with EMT liftoff, material properties, and other factors, using the absolute amplitude measurement may not be reliable. To circumvent these issues, a relative amplitude comparison may be used to determine disbonds. The transmitting and receiving EMAT's are separated by some short fixed distance and all amplitudes are normalized to the "reference pulse" that travels directly from the transmitter to the receiver. In one non-limiting embodiment, the circumferential wave traveling in the counterclockwise direction is the first wave to traverse the entire circumference and is therefore used for coating bond assessment.

Another coating disbond detection feature arises when theoretical modeling results are considered. As provided in group velocity dispersion curves, there is a notable decrease in the maximum velocity at which a group of waves can propagate in a coated pipe as compared to the case of a bare pipe. Additionally, the number of propagating modes in the frequency range of interest increases significantly for the case of a coated pipe. The velocity difference between the bare pipe and the coated pipe cases can be used as a disbond detection feature.

When visco-elastic materials are involved, the attenuation of ultrasound guided waves becomes a frequency dependent problem. In an example embodiment, an elastic layer is assumed and a coating layer is truly visco-elastic and thus there will be some attenuation due to absorption. In the case of guided SH-waves, attenuation increases with frequency. As SH-waves are of primary interest, the tendency of attenuation to increase with frequency can be used as a coating disbond detection feature. The absence of coating will result in a frequency spectrum with higher frequency content. As the amount of well bonded coating increases, higher frequency content will be filtered out by absorption. Single sensor pair and multiple sensor pair systems may be used for amplitude based, time based and frequency based analysis techniques.

In the foregoing specification, the aspects of the invention have been described with reference to specific embodiments thereof. It will, however, be evident that various modifications and changes may be made thereunto without departing from the broader spirit and scope of the invention as set forth in the appended claims. The specification and drawings are accordingly to be regarded in an illustrative rather than in a restrictive sense.

What is claimed is:

1. An ultrasonic guided-wave nondestructive testing method for a pipe, comprising:
   placing an array of transducers on the pipe;
   placing a self-calibrating sensor arrangement on the pipe;
   generating a wave through the transducers from a mode selection routine, operable on a computer for selection of a mode of excitement for the array of transducers;
   receiving the wave through the sensor arrangement and processing the wave through a sensor receiving routine operable on the computer, the computer configured to operate with the self-calibrating sensor arrangement and receive the wave from the array of transducers; and
   processing the wave through the computer with a signal enhancement process; wherein at least one of a bond state of internal and external pipe coatings are characterized through the signal enhancement process and any present coating disbonds are detected and sized approximately.

2. The method according to claim 1, further comprising:
   generating at least one of a guided wave phase velocity and group velocity dispersion curve for both a bare and a coated pipe condition in the processing of the wave, wherein modes with similar wave structures in a pipe wall at a specific frequency are examined for group velocity disparities, and wherein a mode at a frequency is used for evaluation of pipe and coating bond state.

3. The method according to claim 1, wherein properties of the wave are minimally affected by moderate wall thinning, diametral variations, and wetted/soiled interfaces.

4. The method according to claim 1, further comprising:
   generating attenuation dispersion curves for the coated pipe condition, whereby modes exhibiting frequency dependent attenuation are utilized.

5. The method according to claim 1, wherein during the placing of the self-calibrating sensor arrangement, the arrangement is juxtaposed to the array of transmitting transducers, whereby an excited circumferential wave traveling directly toward the arrangement is received, recorded and subsequently used in a normalization routine for subsequently received wave packets.

6. The method according to claim 1, wherein during the placing of the self-calibrating sensor arrangement, a receiving sensor is exactly opposed to a transmitting sensor on the pipe, wherein constructive interference of a clock-wise wave and counter clock-wise propagating wave results in a formation of a single received wave packet, whereby features of a received wave packet are used for characterizing the coating bond state.

7. The method according to claim 1, wherein a change in time-of-flight of a circumferential wave, caused by one of a presence and absence of bonded coating, is used to identify coating disbonds.

8. The method according to claim 1, wherein an amount of one of present and attenuated frequency content in a circumferential wave that has propagated over a distance is used to identify coating disbonds over that distance, wherein the frequency content is measured relative to a reference pulse.

9. The method according to claim 1, wherein a relative amplitude of the received circumferential wave is used to identify coating disbonds over some region through which the wave has propagated.

10. The method according to claim 1, further comprising:
using a spatial averaging method and a time-frequency representation of the received signal to enhance signal quality.

11. The method according to claim 1, wherein a pattern recognition approach for a prediction of defect type, location and estimation of size based on received wave features including at least one of mode conversion phenomena, scattering phenomena, transmission and reflection factors, phase features, and time-of-flight and amplitude features, wherein a presence and value of individual features are combined into a logic algorithm that produces a prediction regarding defect type, location and one or more of the defect dimensions.

12. The method according to claim 1, wherein the coating disbond and a defect axial length sizing algorithms use one of a sorting and fuzzy logic algorithm to account for corrosion growth beyond the coating debonding.

13. The method according to claim 1, wherein at least one of an inside and an outside of the pipe is characterized.

14. The method according to claim 4, wherein the mode selection routine chooses a frequency with a dependent attenuation that exhibits entirely one of an increasing and entirely decreasing attenuation over a utilized frequency bandwidth.

15. The method according to claim 5, wherein a same receiving sensor, utilized for normalization, is utilized to receive all subsequent wave packets.

16. The method according to claim 5, further comprising:
using a second receiving sensor to receive wave packets originating from a specific portion of the pipe circumference, wherein multiple sensor sets are used for full circumferential inspection.

17. The method according to claim 5, wherein in the normalization routine, at least one of the arrival time, amplitude, frequency content, and phase of the received wave are utilized for normalization of subsequently received wave packets.

18. The method according to claim 6, wherein during the processing of the wave a presence of multiple peaks indicates an existence of a coating anomaly, wherein a disparity in one of a time-of-arrival, amplitude, frequency content, and phase of the clock wise and counter clock wise traveling wave is used to characterize the coating bond.

19. The method according to claim 10, wherein a signal acquired at a current acquisition location is averaged with that of one of several backward locations, several forward locations, and both several backward and forward locations, whereby a signal-to-noise ratio of the signal acquired at the current location is improved with at least one of use of time averaging and without a use of time averaging.

20. The method according to claim 10, wherein one of a short-time Fourier Transform, and other similar time-frequency representations, is used enabling an identification of low-amplitude pulses otherwise embedded in noise of a time-amplitude representation.

* * * * *